(12) United States Patent
Piskun

(10) Patent No.: US 6,454,783 B1
(45) Date of Patent: *Sep. 24, 2002

(54) LAPAROSCOPIC INSTRUMENTS AND TROCAR SYSTEMS FOR TRANS-UMBILICAL LAPROSCOPIC SURGERY

(76) Inventor: Gregory Piskun, 434 Shady Ave., Apt. 18, Pittsburg, PA (US) 15206

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/397,630

(22) Filed: Sep. 15, 1999

(51) Int. Cl.[7] ............................................. A61B 17/34
(52) U.S. Cl. ..................................... 606/185; 606/1
(58) Field of Search ...................... 606/185, 1, 144; 604/164.03, 174

(56) References Cited

U.S. PATENT DOCUMENTS

| | | | |
|---|---|---|---|
| 2,669,991 A | * | 2/1954 | Curutchet |
| 4,644,951 A | * | 2/1987 | Bays |
| 4,863,430 A | * | 9/1989 | Klyce et al. ................. 604/164 |
| 5,242,409 A | * | 9/1993 | Buelna |
| 5,549,563 A | * | 8/1996 | Kronner |
| 5,964,781 A | * | 10/1999 | Mollenauer et al. ......... 606/213 |

* cited by examiner

Primary Examiner—Michael H. Thaler
(74) Attorney, Agent, or Firm—R. Neil Sudol; Henry Coleman; William Sapone

(57) ABSTRACT

Laparoscopic instruments and trocars are provided for performing laparoscopic procedures entirely through the umbilicus. A generally C-shaped trocar provides increased work space between the hands of the surgeon as well as S-shaped laparoscopic instruments placed through the trocar when laparoscopic instrument-trocar units are placed through the umbilicus. In order to facilitate retraction of intra-abdominal structures during a laparoscopic procedure, an angulated needle and thread with either one or two sharp ends is provided. Alternatively, an inflatable unit having at least one generally C-shaped trocar incorporated within the unit's walls can be placed through the umbilicus following a single incision. Generally S-shaped laparoscopic instruments may be placed through the generally C-shaped trocars to facilitate access to intra-abdominal structures.

14 Claims, 4 Drawing Sheets

LAPAROSCOPIC INSTRUMENTS AND TROCAR SYSTEMS FOR TRANS-UMBILICAL LAPROSCOPIC SURGERY

FIELD OF THE INVENTION

The present invention relates to surgical instruments, and particularly to laparoscopic instruments which facilitate the performance of laparoscopic procedures entirely through the umbilicus.

BACKGROUND INFORMATION

Abdominal laparoscopic surgery gained popularity in the late 1980's, when benefits of laparoscopic removal of the gallbladder over traditional (open) operation became evident. Reduced post-operative recovery time, markedly decreased post-operative pain and wound infection, and improved cosmetic outcome are well established benefits of laparoscopic surgery, derived mainly from the ability of laparoscopic surgeons to perform an operation utilizing smaller incisions of the body cavity wall.

Laparoscopic procedures generally involve insufflation of the abdominal cavity with $CO_2$ gas to a pressure of around 15 mm Hg. The abdominal wall is pierced and a 5–10 mm in diameter straight tubular cannula or trocar is then inserted into the abdominal cavity. A laparoscopic telescope connected to an operating room monitor is used to visualize the operative field, and is placed through one of the trocars. Laparoscopic instruments (graspers, dissectors, scissors, retractors, etc.) are placed through two or more additional trocars for the manipulations by the surgeon and surgical assistant(s).

Generally, one or two trocars are used by the surgeon (active trocars), while one or two additional trocars are utilized by a surgical assistant for organ and/or tissue retraction (passive trocars). For example, laparoscopic cholecystectomy (gallbladder removal) is generally performed using four trocars: one is placed in the umbilicus (belly button) for a telescope, a second is inserted approximately 3 inches above the umbilicus for use as an active trocar by the surgeon, and two additional passive trocars are positioned on the right side of the abdomen to enable a surgical assistant to retract the gall bladder. As a result of this procedure, the gall bladder is extracted through the umbilicus.

It is often required to increase the umbilical incision to 2–3 cm or more to accommodate a thick, enlarged gall bladder. As a result, the incision and subsequent scar in the umbilicus is not visible, however, the three non-umbilical incisions leave permanent 5–10 mm scars. In addition, the non-umbilical incisions are a source of potential complications including bleeding, infection, scar formation, and pain. Recently, so-called "mini-laparoscopy" has been introduced utilizing 2–3 mm diameter straight trocars and laparoscopic instruments. When successful, mini-laparoscopy allows further reduction of abdominal wall trauma and improved cosmesis. However, instruments used for mini-laparoscopic procedures are very expensive and fragile. Because of their poor durability, mini-laparoscopic instruments can be used only on patients with very thin abdominal walls, which represents a small percentage of patients requiring an abdominal laparoscopic procedure. In addition, 2–3 mm scars, although small, still may be a source of an undesirable cosmetic outcome and potential wound complications. Further, some patients develop keloid or hypertrophic scar tissue formation even using 2–3 mm incisions.

When conventional trocars and conventional laparoscopic instruments are inserted only through the umbilicus of the patient, the close proximity of the instruments to each other results in the so-called "chopstick effect", which is a significant limitation to the manipulation of conventional laparoscopic instruments through conventional trocars. This "chopstick effect" describes the interference between the surgeon's hands as well as the interference between the laparoscopic instruments. Laparoscopic procedures require complex movements within three-dimensional space, including both the workspace inside the patient's abdominal cavity and the area outside the patient's abdominal cavity occupied by the proximal portions of the laparoscopic instruments and the surgeon's hands. When the handles for laparoscopic instruments and the surgeon's hands are immediately adjacent to each other, as is the case in conventional laparoscopic procedures, the surgeon's left and right hands inevitably make contact. In addition, contact between each of the instrument's shafts can occur. This contact markedly restricts the movement of the surgeon's hands of each instrument, both separately and in relation to each other, hence greatly reducing the surgeon's ability to perform a described procedure and significantly increasing the skill level needed to perform the procedure.

Thus, there is a need for instruments and trocar systems which allow laparoscopic procedures to be performed entirely through the umbilicus while at the same time reducing or eliminating the above-described "chopstick effect". Performance of a laparoscopic procedure entirely through the umbilicus using the laparoscopic instruments and trocar system according to an embodiment of the present invention can improve significantly the surgeon's access to various abdominal structures and the cosmetic outcome of laparoscopic procedures, while reducing the degree of operative and post-operative complications.

SUMMARY OF THE INVENTION

The present invention provides laparoscopic instruments and trocars for the performance of laparoscopic procedures entirely through the umbilicus.

An object of the present invention is to provide a laparoscopic instrument-trocar unit, which markedly increases the work space between the hands of the surgeon when the laparoscopic instrument-trocar units are placed through the umbilicus.

An additional object of the present invention is to provide a generally C-shaped trocar, which facilitates reduction in the interference between manipulated laparoscopic instruments.

Another object of the present invention is to provide generally S-shaped laparoscopic instruments, where the proximal curve of "S" corresponds to the "C" curve of the C-shaped trocar creating separation between manually controlled ends of the laparoscopic instruments, while the distal curve of the "S" creates a markedly increased work space between laparoscopic instruments.

Another object of the present invention is to provide a stretchable and inflatable generally C-shaped trocar for accommodation of the rigid generally S-shaped laparoscopic instruments, which, when inflated creates a single unit with an S-shaped instrument.

Another object of the present invention is to provide an inflatable unit with at least one generally C-shaped trocar incorporated within the unit's walls, which can be placed through the umbilicus following a single incision.

Another object of the invention is to provide an angulated needle with two sharp ends and a thread attached to the angle of the needle for use in organ retraction, which allows penetration of the abdominal wall, an intra-abdominal structure, and then the abdominal wall again without a change in the orientation of the needle.

A further object of the present invention is to provide an angulated needle having a long segment on one side of the angle which terminates in a sharp point and a shorter segment on the other side of the angle which has a thread attached to it.

According to an exemplary embodiment of the present invention, laparoscopic instruments and trocars are provided for performing laparoscopic procedures entirely through the umbilicus. A generally C-shaped trocar markedly increases the work space between the hands of the surgeon thereby reducing interference between the surgeon's hands as well as the manipulated laparoscopic instruments, particularly when the laparoscopic instrument-trocar units are placed through the umbilicus. In order to facilitate retraction of intra-abdominal structures during a laparoscopic procedure, an angulated needle and thread with either one or two sharp ends is provided. Alternatively, an inflatable unit having at least one generally C-shaped trocar incorporated within the unit's walls can be placed through the umbilicus following a single incision. Generally S-shaped laparoscopic instruments may be placed through the generally C-shaped trocars to facilitate access to intra-abdominal structures.

DETAILED DESCRIPTION

Figure 1:
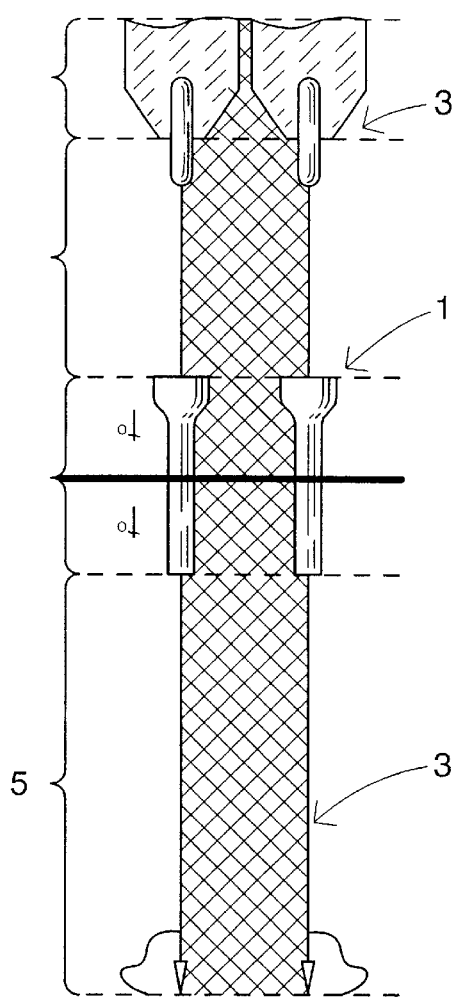
FIG. 1 is a schematic view of a conventional laparoscopic instrument inserted through a conventional straight trocar.

The present invention provides laparoscopic instruments and trocars for the performance of laparoscopic procedures entirely through the umbilicus. Referring now in specific detail to the drawings, in which like reference numerals identify similar or identical elements, there is shown in FIG. 1 a conventional prior art laparoscopic instrument—trocar assembly.

As illustrated in FIG. 1, a conventional trocar 1 is an essentially straight, hollow instrument, which allows conventional laparoscopic instruments 3 such as an endoscope of suitable diameter to be inserted through the conventional trocar 1 and into the abdominal cavity 5 of a patient. Conventional trocars 1 have a diameter of around 2–15 mm. Once the conventional laparoscopic instruments 3 are in place, standard laparoscopic procedures may be performed, such as cholecystectomy, appendectomy, or simple diagnostic laparoscopy.

As shown in FIG. 1, when conventional trocars 1 and conventional laparoscopic instruments 3 are inserted only through the umbilicus of the patient, the close proximity of the instruments to each other results in the so-called chopstick effect, which is a significant limitation to the manipulation of conventional laparoscopic instruments 3 through conventional trocars 1.

Figure 2A:
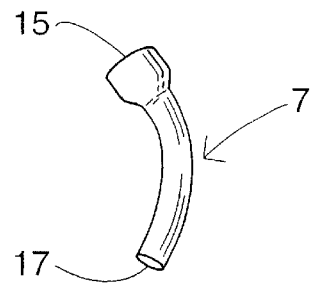
FIG. 2A is a side view and FIG. 2B is an end view of an exemplary embodiment of a flexible C-shaped trocar.
Figure 2B:

As shown in FIG. 2A and FIG. 2B, an exemplary C-shaped trocar 7 according to an embodiment of the present invention is generally an elongated tube having a proximal end 15 and a distal end 17. In one exemplary embodiment the C-shape curve through ends 15, 17 is bent so that each end portion forms an angle of approximately 30° with respect to a tangent to the center of the trocar 7. However, any angle which sufficiently reduces the chopstick effect may be used. Thus, exemplary embodiments of the present invention with angles from 5–45° may be used. A C-shaped trocar 7 may be made of conventional material as is known in the art. The interior diameter of a C-shaped trocar 7 is preferably around 5 mm. However, in alternate embodiments the interior diameter of the C-shaped trocar 7 may range from 2–15 mm. In one exemplary embodiment, the C-shape is relatively fixed and does not vary, for example when the trocar 7 has a rigid composition. In an alternate exemplary embodiment, the C-shaped trocar 7 is more flexible allowing the surgeon or surgical assistant to bend the trocar 7 changing the angle of the C-shape, for example via insertion of an instrument into the trocar.

Figure 2C:
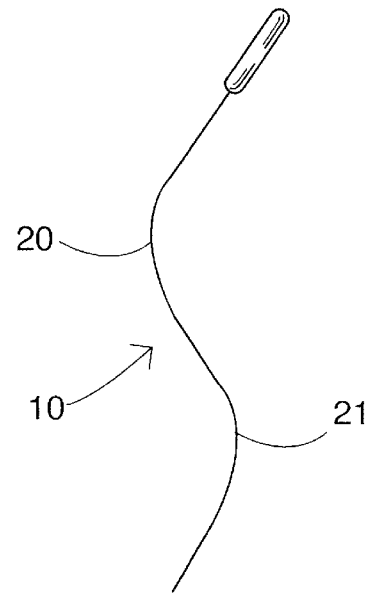
FIG. 2C is an exemplary embodiment of an S-shaped instrument.

FIG. 2C illustrates an exemplary S-shaped laparoscopic instrument 10 in accordance with an embodiment of the present invention. The S-shaped laparoscopic instrument 10 has, for example, a proximal curve 20 and a distal curve 21. Examples of laparoscopic instruments 10 which can be formed generally into an S-shape according to an embodiment of the present invention include but are not limited to scissors, clamps, dissectors, staplers, clip appliers, retrieval bags, and electrocautery instruments. The S-shape for these instruments can be achieved, for example, by using conventional manufacturing techniques modified to accommodate the S-shape contour of the instrument.

Figure 3:
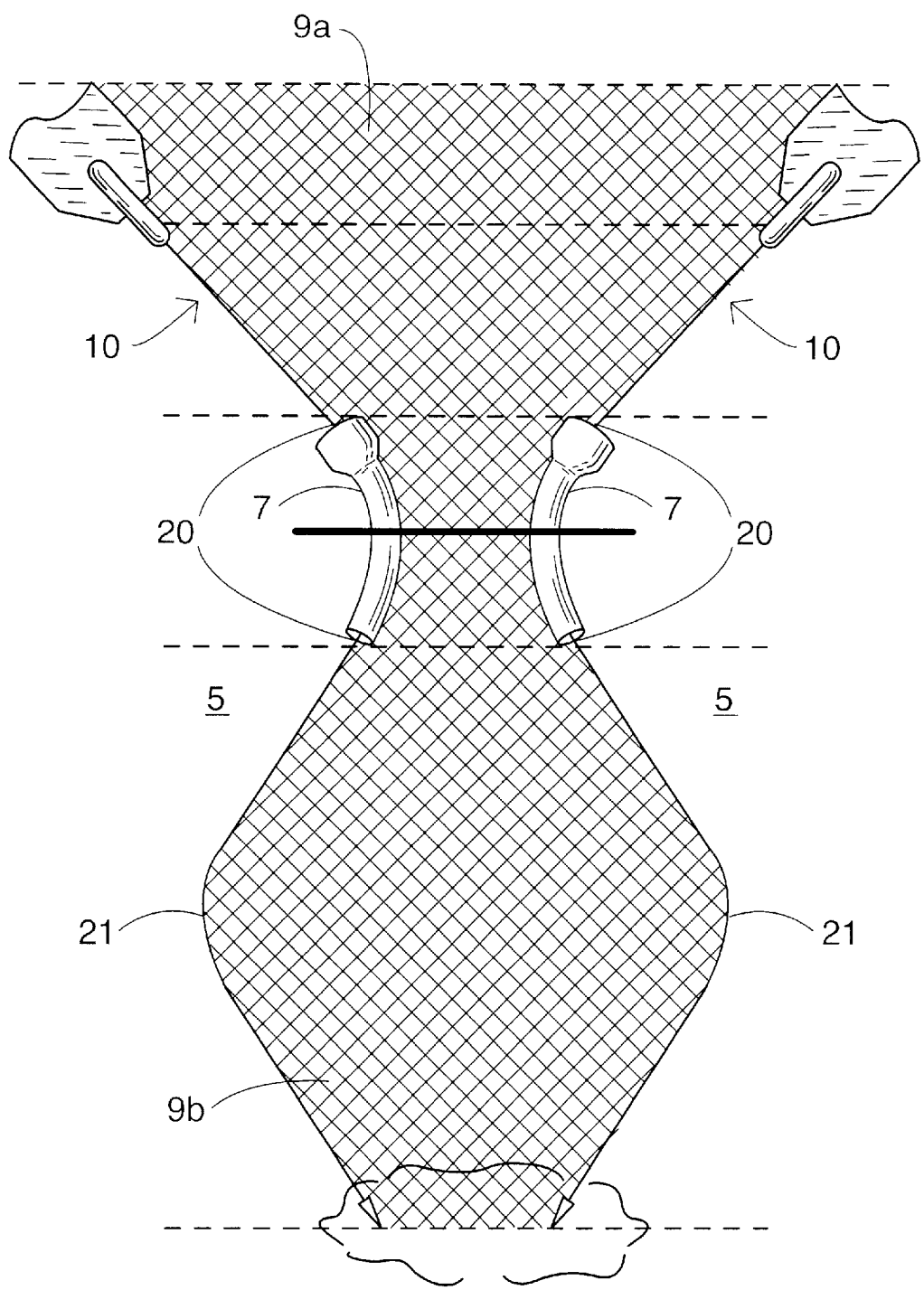
FIG. 3 is a schematic view of an exemplary embodiment of an S-shaped laparoscopic instrument inserted through a C-shaped flexible trocar.

As illustrated in FIG. 3, a generally S-shaped laparoscopic instrument 10 may be inserted through a C-shaped trocar 7. For example, the proximal curve 20 of the S-shaped instrument 10 corresponds to the curve of the C-shaped trocar 7. The distal curve 21 of the S-shaped instrument 10 also corresponds to the curve of the C-shaped trocar 7 and when inserted through the C-shaped trocar 7 will be, for example, entirely within the abdominal cavity 5 of the patient. An embodiment of the present invention, for example, a C-shaped trocar 7 and S-shaped laparoscopic instrument 10 allows the surgeon to perform the laparoscopic procedure without making incisions outside of the umbilicus. In accordance with the present invention, the size and curvature of a C-shaped trocar 7 will correspond to the size and curvature of an S-shaped instrument 10 and can include any desired size.

This arrangement of C-shaped trocar 7 and S-shaped instrument 10 eliminates the "chopstick effect" which results from the insertion of conventional laparoscopic instruments 3 through the umbilicus. For example, the proximal curves of the S-shaped instruments 10 and the C-shaped trocar 7 allows the surgeon's hands and the proximal portions of the instruments 20, including the instruments' handles, to be placed as far apart as is convenient for the surgeon. For example, workspace 9a is created. Movement of the proximal portion of one instrument 20 away from the proximal portion 20 of the other also markedly separates the exposed (e.g. outside the body cavity) shafts of each instrument. The distal curve of the S-shaped instrument 21 creates workspace 9b between the portions of the instruments in the abdominal cavity and redirects the distal end of the laparoscopic instrument 10 back toward a target site 8, such as an abdominal organ or other abdominal structure or site.

Thus, an S-shaped laparoscopic instrument 10 may be thought of as having four segments or sections to allow an abdominal procedure to be performed entirely through the umbilicus and yet overcome the "chopstick effect" encountered with conventional laparoscopic instruments 3 and trocars 1. First, the portion outside of the patient's abdominal cavity 5 allows sufficient space between the surgeon's hands when manipulating the proximal portion of the laparoscopic instruments 10. Second, the portion at or near the umbilicus, which allows a laparoscopic instrument 10 to enter the abdominal cavity 5 is in close proximity to one or more additional laparoscopic instruments 10 so that all instruments 10 enter the abdomen through the umbilicus. Third, the portion beyond the second portion which creates separation between laparoscopic instruments 10 within the abdominal cavity 5. Fourth, the distal end of a laparoscopic instrument 10 is shaped to point back toward the target abdominal organ, tissue, or other site.

Examples of procedures which can be facilitated by the use of C-shaped trocars 7 and S-shaped laparoscopic instruments 10 include, but are not limited to diagnostic laparoscopy, cholecystectomy, appendectomy, ovarohysterectomy, removal of a section of bowel, a variety of gastric procedures, biopsy of various abdominal organs including the liver, laparoscopic staging for cancer, and hernia repair.

The following discussion describes, as an example, a cholecystectomy procedure according to an embodiment of the present invention as described in FIGS. 2A–C and FIG. 3. It should be noted, however, that many other laparoscopic procedures may be performed using various embodiments of applicant's invention. The following description, therefore, is merely illustrative and is not intended to limit the present invention to the description given in this example.

A laparoscopic procedure, such as a cholecystectomy, using a curved C-shaped flexible or rigid trocar 7 and S-shaped laparoscopic instruments 10 of the present invention is performed with the patient under general anesthesia. Carbon dioxide gas is insufflated intra-abdominally to 15 mm Hg through a 5 mm lateral umbilical incision using, for example, a VERESS™ needle. For example, two curved C-shaped 5 mm trocars 7 are then inserted through an incision in the umbilicus. The surgeon operates, for example, a 5 mm endoscope with one hand and a 5 mm S-shaped laparoscopic instrument 10 with the other, each of which are passed through a respective trocar 7. The trocar for the endoscope could be straight so that a conventional straight endoscope could be used, the other curved trocar 7 providing separation between the instruments and the surgeon's hands. Pericholecystic adhesions, if present, are removed by blunt or sharp dissection using an S-shaped dissector to expose the dome of the gallbladder. A 2-0 nylon (or other suitable material) stay suture on a needle is placed through the abdominal wall immediately below the right costal margin at the right anterior axillary line, allowing for superior retraction of the gall bladder dome. The removal of the adhesions from around the gallbladder infundibulum is then continued as necessary. A second stay suture is placed through the right flank and then through the neck of the gallbladder allowing for lateral retraction to expose the cystic structures. The cystic duct and cystic artery are dissected, then ligated with clips, utilizing a 5 mm S-shaped clip applier, and then finally transected with a S-shaped scissors. With continued retraction from stay sutures, the gallbladder is removed from the liver bed utilizing an S-shaped electrocautery device equipped with a hook, dissecting the gallbladder from medial to lateral and inferior to superior direction. The perihepatic area is then irrigated using an S-shaped irrigation/suction device.

The above-described procedure is greatly facilitated by the use of S-shaped laparoscopic instruments 10 and C-shaped trocars 7, allowing the procedure to be performed entirely through the umbilicus while at the same time reducing or eliminating the "chopstick effect". For example, each of the S-shaped laparoscopic instruments is inserted and removed from the active curved trocar 7 as needed during the procedure and conflict with the endoscope is avoided. Thus, as a result, improved cosmesis, reduced operative and post-operative complications, and a less complicated surgical technique is achieved.

Figure 4A:
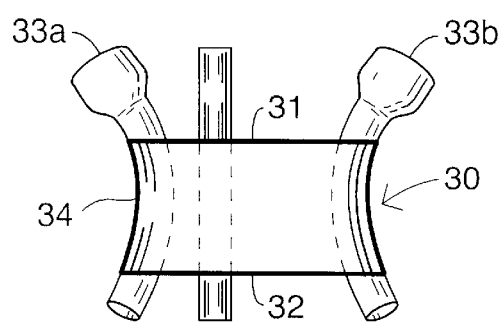
FIG. 4A is a lateral view and FIG. 4B is a perspective view of an exemplary inflatable unit with multiple C-shaped trocars incorporated within the unit.
Figure 4B:
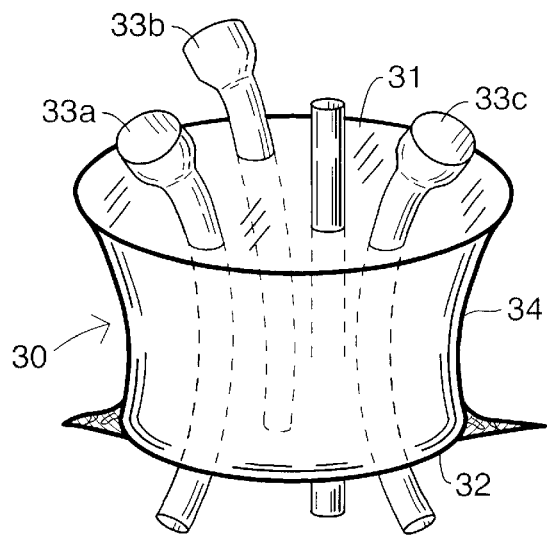

FIG. 4A and FIG. 4B illustrate an inflatable unit 30 having, for example, multiple C-shaped trocars incorporated within the unit 30. The lateral wall 34 of the inflatable unit 30 may vary from extremely flexible and stretchable when deflated, thus facilitating insertion into the umbilical incision, to somewhat rigid when inflated during the surgical procedure. The inflatable unit 30 has, for example, a horizontal upper plate 31 and a horizontal lower plate 32. The trocar will extend through the horizontal upper plate 31 and horizontal lower plate 32 and may be incorporated within the lateral wall 34. Rigid sections may be inserted or attached around the periphery of the horizontal upper 31 or lower 32 plate to add stability. The horizontal upper plate 31 and horizontal lower plate 32 may be, for example concave or straight. At least one and possibly two or more C-shaped trocars 33a, 33b, 33c (described previously) can be incorporated within the lateral wall 34 of the inflatable unit 30 and are distributed, for example, evenly around the wall 34 of the unit 30. The upper 31 and lower plate 32 are preferably made of a flexible plastic material or other suitable surgical quality material.

In an alternate embodiment, the inflatable unit 30 has one or more C-shaped trocars 7 incorporated within its lateral wall 34, and one or more straight trocar 1, also incorporated within the inflatable unit's lateral wall 34. The straight trocar may accommodate, for example, a straight endoscopic or laparoscopic instrument, while the C-shaped trocars 7 can accommodate an S-shaped instrument 10 as described above. Thus, even where one of the instruments is relatively straight and passes through a relatively straight trocar 1, the chopstick effect is still reduced as a result of the remaining C-shaped trocars 7 and S-shaped instruments 10, which provide space between the surgeons hands, the proximal portions of laparoscopic instruments (which includes the straight laparoscope), and the distal ends of the laparoscopic instruments (which also includes the straight laparoscope).

The surgeon may place the inflatable unit 30 through an approximately 1.5 to 2.5 cm incision in the umbilicus. The unit 30 is inserted prior to inflation with the C-shaped trocars 33a, 33b, 33c, for example, parallel and in close proximity to each other. The upper plate 31 will remain outside of the umbilicus while the lower plate 32 is located just inside the abdominal cavity 5. Once the unit 30 is properly positioned, the surgeon or assistant may inflate the unit 30. The unit 30 may be inflated via, for example, a one-directional valve using a syringe or gas line inserted into a narrow hollow tube connected to the unit 30 as is known in the art. The syringe or gas line may be alternatively inserted directly into a one-directional valve. Thus, means for inflating the unit 30 can be similar to the means for inflating a conventional endotracheal tube.

In an exemplary embodiment, the diameter of the inflatable unit 30 increases upon inflation. The unit may be inflated to the extent needed for the particular laparoscopic procedure. By placing the trocars in the lateral walls of the inflatable unit, the surgeon may position a trocar, and thus an instrument inserted through a trocar, as far away from the other trocars and instruments as possible within the confines of a chosen space such as the umbilicus. In addition, the surgeon may change the position of the trocars and instruments within the umbilicus by rotating the inflatable unit 30 around its vertical axis. This change of position of the trocars allows intra-operative adjustments of the position of an instrument. as well as the type of instrument to further facilitate the intra-abdominal procedure. Moreover, the inflatable unit 30 seals the opening of the patient's abdominal cavity 5 to prevent leakage of $CO_2$ as a result of the inflation.

Figure 8:
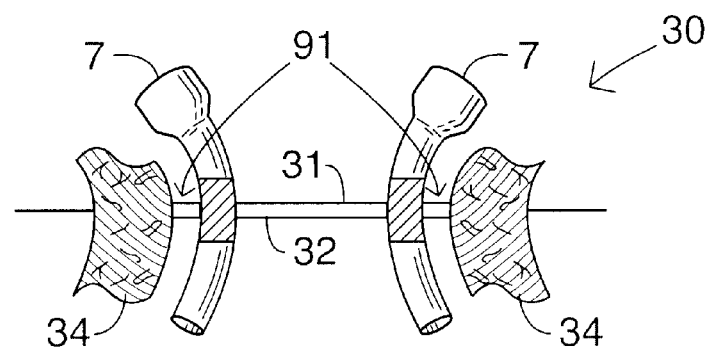
FIG. 8 is a cross-sectional view of an exemplary embodiment of an inflatable unit having multiple trocars incorporated within the unit.

In an alternate embodiment as shown in FIG. 8, the distance between the upper plate 31 and the lower plate 32 may be reduced, thereby increasing the ability of the trocar 7 to move in relation to the wall of the inflatable unit 30. In addition, reducing the distance between the upper plate 31 and lower plate 32 allows the size of the trocars incorporated within the unit 30 to be reduced, which further enhances the ability of the trocar to move in relation to the wall of the inflatable unit 30. In one exemplary embodiment, the trocar is immediately adjacent to the lateral wall 34. In another exemplary embodiment the trocar is not immediately adjacent to the lateral wall 34, but is separated by an additional connector 91 to provide even greater flexibility.

Thus, as an example, the cholecystectomy procedure described above may be performed using the inflatable unit 30 in conjunction with S-shaped laparoscopic instruments 10, rather than using separate trocar/instrument arrangements. Once the gallbladder is transected and removed from the liver bed, it is removed through the 1.5 to 2.5 mm incision along with the inflatable unit 30. If necessary, the initial incision can be extended to remove an enlarged gallbladder. Alternatively, the gallbladder may be opened to remove or crush material present in the gallbladder such as gallstones, facilitating removal of the gallbladder and the inflatable unit 30 through the umbilical incision.

Figure 5A:
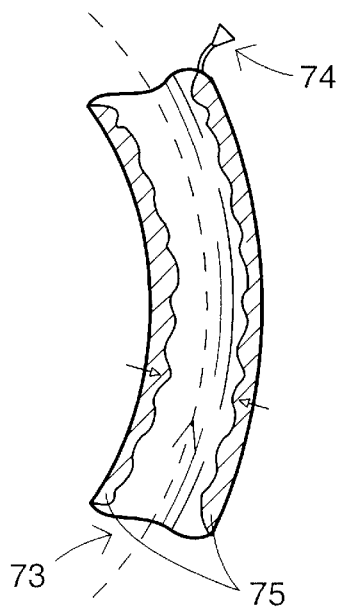
FIG. 5A is a non-inflated lateral view and FIG. 5B is an inflated lateral view of a exemplary inflatable C-shaped trocar having a balloon-like structure within the hollow body of the trocar.
Figure 5B:
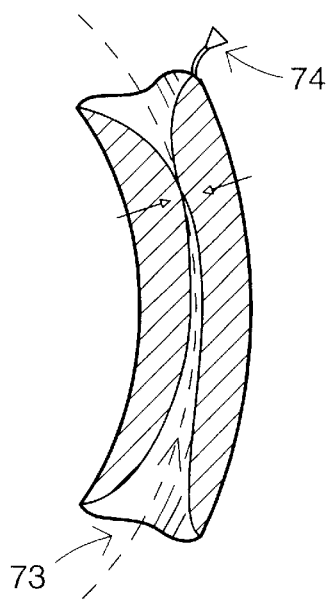

As shown in FIG. 5A and FIG. 5B, an alternate exemplary embodiment of the present invention provides an inflatable unit 70 including a single C-shaped trocar 7 having a radially expandable and inflatable balloon-like structure 75 incorporated within the hollow lumen 73 of the trocar. A single laparoscopic instrument may be inserted within this inflatable unit 70. This unit 70 may then be inflated to secure the trocar and laparoscopic instrument together as one movable unit. The inflatable unit 70 may be inflated via, for example, a one-directional valve using a syringe or gas line inserted into a narrow hollow tube 74 connected to the unit 70 as is known in the art. The syringe or gas line may be alternatively inserted directly into a one-directional valve. Thus, means for inflating the unit 70 can be similar to the means for inflating a conventional endotracheal tube. Inflating the inflatable unit 70 also serves to seal the abdomen preventing insufflated gas from escaping through the lumen of the trocar. The inflatable unit 70 then may be deflated, the laparoscopic instrument may be removed, and a different instrument may be inserted.

While the above description of S-shaped instruments 10 and C-shaped trocars 7 has been directed to procedures performed entirely through the umbilicus, it is to be understood that embodiments of the present invention may be adapted for use in other entry sites. Therefore, when it is desirable to have entry of multiple instruments in a relatively localized area, embodiments of the present invention may be used for such entry, while reducing or eliminating the so-called "chopstick effect". Thus, existing scars or hidden areas such as the pubic hair line or the axillary region may be used as a localized entry site. Procedures such as repair of a ventral hernia may be performed using a non-umbilical localized entry site.

Figure 6:
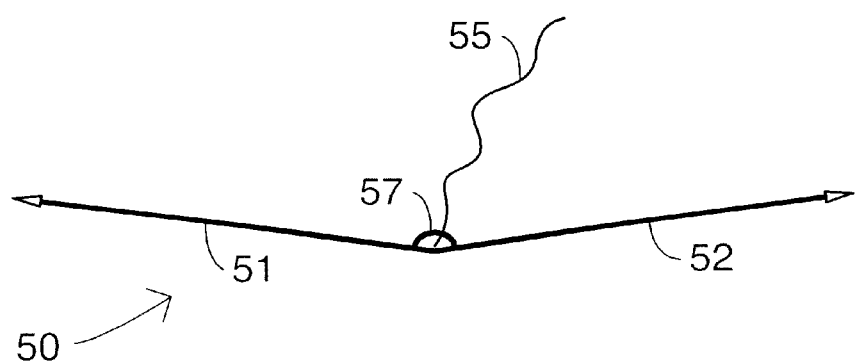
FIG. 6 is a lateral view of an exemplary angulated needle with two sharp ends and a thread attached at the angle of the needle.

As illustrated in FIG. 6, an angulated bi-directional needle 50 in accordance with the present invention is provided with a first sharp end 51, a second sharp end 52, and a surgical thread 55 attached to the angle 57 of the needle 50. The needle 50 has, for example, a total length of around 5–10 cm. The length of each segment from angle to sharp end is roughly equivalent, but need not be. An acute angle of around 160° is formed by the angulated needle 50, however angles 57 ranging from a straight needle, i.e. 180°, to an acute angle 57 of around 90° may be used. The needle is formed out of steel or other suitable material. The surgical thread 55, such as 2-0 nylon, is attached at the angle 57 of the needle 50.

The angulated needle 50 according to an embodiment of the present invention simplifies suture delivery through the gall bladder or other abdominal structure. For example, the first sharp end 51 of the needle 50 is inserted through the body wall by the surgeon. The needle 50 is then grasped within the abdominal cavity 5 by a laparoscopic instrument under endoscopic guidance and is pulled toward the organ of interest. With the second sharp end 52 leading, a stitch is placed through the abdominal structure of interest. The second sharp end 52 is then delivered through the abdominal wall.

The angulated bi-directional needle 50 allows delivery of a stitch without changing the orientation of the sharp end as would be necessary if a needle with only one sharp end is used. Changing orientation of a needle with only one sharp end is a somewhat complicated task requiring advanced laparoscopic skills and may result in iatrogenic injury. In addition, the angulated bi-directional needle 50 can be used to reposition a gall bladder or other structure during a laparoscopic procedure by pulling or relaxing the suture, eliminating or reducing the need for the insertion of one or more additional trocars and laparoscopic instruments for that purpose.

Figure 7:
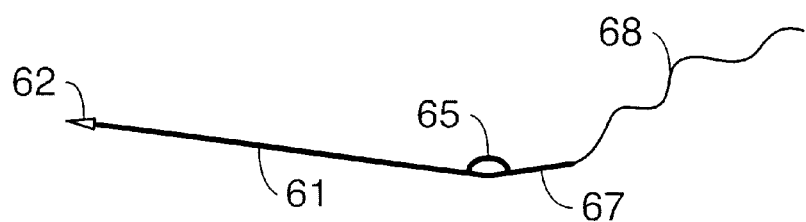
FIG. 7 is a lateral view of an exemplary angulated needle having a long segment with a pointed end on one side of the angle and a short segment having attached thread on the other side of the angle.

An alternative exemplary embodiment of an angulated needle is shown in FIG. 7. In this embodiment the angulated needle 60 has, for example, a long segment 61 with one sharp end 62 on one side of the angle 65. The needle 60 has a blunt short segment 67 on the other side of the angle 65. Thread 68 is attached to the end of the blunt short segment 67.

The angulated needle 60 allows penetration through the body wall as a straight needle. The needle 60 is inserted into and through the wall of the gallbladder. The needle is then flipped 180° and delivered back through the abdominal wall.

The angulated needle 60 can be used to reposition a gall bladder or other structure during a laparoscopic procedure by, for example, pulling or relaxing the suture, which eliminates or reduces the need for the insertion of one or more additional trocars and laparoscopic instruments for that purpose. The angulation of the angulated needle 60 also reduces the chance of iatrogenic injury to surrounding structures by allowing the needle 60 to be flipped and then delivered back through the abdominal wall prior to contacting surrounding abdominal structures.

While several exemplary embodiments of laparoscopic instruments and trocars for the performance of laparoscopic procedures entirely through the umbilicus have been described herein, it is to be understood that variations may be made in the laparoscopic instruments and trocars without departing from the spirit and scope of the present invention as defined by the appended claims.

What is claimed is:

1. A surgical instrument system comprising a trocar assembly and a laparoscopic surgical instrument, the trocar assembly comprising:
    an upper surface;
    a lower surface disposed below the upper surface;
    an outer wall connected between the upper surface and the lower surface, a chamber being enclosed within outer wall; and
    at least one curved trocar sleeve or cannula disposed through the upper surface and the lower surface, the trocar sleeve or cannula comprising:
        a first end portion;
        a curved center portion connected to the first end portion; and
        a second end portion connected to the curved center portion, the first end portion, curved center portion, and second end portion having an opening disposed therethrough, the first end portion and second end portion each forming an acute angle with respect to a tangent to the curved center portion, wherein the opening is capable of releasably receiving a curved instrument, the first end portion, curved center portion and second end portion providing a first orientation direction for an upper portion of the curved instrument and a second orientation direction for a lower portion of the curved instrument,
        the laparoscopic surgical instrument being an S-shaped instrument with a preformed S-shaped shaft, the shaft being inserted through the trocar sleeve or cannula.

2. The surgical instrument system of claim 1, wherein the outer wall is flexible.

3. The surgical instrument system of claim 1, further comprising at least one generally straight trocar sleeve or cannula disposed through the upper surface and the lower surface.

4. The surgical instrument system of claim 3, wherein the at least one generally straight trocar sleeve or cannula includes an opening to releasably receive a generally straight instrument.

5. The surgical instrument system of claim 4, wherein the generally straight instrument is a laparoscope.

6. The surgical instrument system of claim 1, wherein a perimeter of at least one of the upper surface and the lower surface is rigid.

7. A method for performing a surgical procedure comprising:
    (A) making an opening into a body cavity of a patient;
    (B) inserting a trocar assembly into the opening, wherein the trocar assembly includes:
        (i) an upper surface,
        (ii) a lower surface disposed below the upper surface,
        (iii) an outer wall connected between the upper surface and the lower surface, a chamber being enclosed within the outer wall, and
        (iv) at least one curved trocar sleeve or cannula disposed through the upper surface and the lower surface;
    (C) inserting, through the trocar sleeve or cannula, a surgical instrument having a preformed S-shaped shaft; and
    (D) after inserting of the surgical instrument through the trocar sleeve or cannula operating the surgical instrument to complete the surgical procedure.

8. A method for performing a surgical procedure, comprising:
    making an opening into a body cavity of a patient;
    providing at least two cannulas or trocar sleeves, at least one of said cannulas or trocar sleeves being curved or arcuate in form with an outer surface which is concave on one side and convex on an opposite side;
    inserting said at least two cannulas or trocar sleeves through said opening so that said two cannulas or trocar sleeves traverse said opening and are partially inside said body cavity and partially outside of the patient;
    providing at least two laparoscopic type surgical instruments, at least one of said surgical instruments having a preformed S-shaped shaft; and
    after the inserting of said cannulas or trocar sleeves through said opening, passing said surgical instruments through respective ones of said cannulas or trocar sleeves so that said surgical instruments traverse the respective ones of said cannulas or trocar sleeves and are partially inside said body cavity and partially outside of the patient, the surgical instrument having said S-shaped shaft being passed through the cannula or trocar sleeve which is curved or arcuate in form with an outer surface which is concave on one side and convex on an opposite side.

9. The method of claim 8 wherein said at least two cannulas or trocar sleeves are each curved or arcuate in form with an outer surface concave on one side and convex on an opposite side, the inserting of said at least two cannulas or trocar sleeves through said opening including manipulating said cannulas or trocar sleeves so that the concave sides of said cannulas or trocar sleeves face outwardly from said opening and the convex sides of said cannulas face inwardly into said opening.

10. The method of claim 9 wherein said at least two laparoscopic surgical instruments each have a preformed S-shaped shaft, further comprising positioning said surgical instruments so that (a) proximal ends of said surgical instruments are substantially spaced from one another, (b) proximal middle portions of said surgical instruments are disposed proximately to one another so as to pass through respective ones of said cannulas or trocar sleeves in said opening, (c) distal middle portions of said surgical instruments are spaced from one another inside said body cavity, and (d) distal tips of said surgical instruments are pointed back towards a target surgical site inside said body cavity.

11. The method of claim 10 wherein said at least two trocar sleeves are parts of a preformed trocar assembly including a body member having an upper surface, a lower surface and a flexible outer surface, the inserting of said cannulas or trocar sleeves through said opening including positioning said trocar assembly in said.

12. The method of claim 8 wherein said at least two trocar sleeves are parts of a preformed trocar assembly including a body member having an upper surface, a lower surface and a flexible outer surface, the inserting of said cannulas or trocar sleeves through said opening including positioning said trocar assembly in said opening.

13. A method for performing a surgical procedure, comprising:

making an opening into a body cavity of a patient;

providing a cannula or trocar sleeve which is curved or arcuate in form with an outer surface which is concave on one side and convex on an opposite side;

inserting said cannula or trocar sleeve through said opening so that said cannula or trocar sleeve traverses said opening and is partially inside said body cavity and partially outside of the patient;

providing a laparoscopic type surgical instrument having a shaft with a preformed inherently C-shaped section, said surgical instrument further having an operative tip;

after the inserting of said cannula or trocar sleeve through said opening, passing said surgical instrument through said cannula or trocar sleeve so that said surgical instrument traverses said cannula or trocar sleeve and is partially outside of the patient and so that said operative tip is inside said body cavity; and after the passing of said surgical instrument through said cannula or trocar sleeve, manipulating said surgical instrument to place said operative tip into effective contact with internal body tissues substantially spaced from cannula or trocar sleeve.

14. The method of claim 13 wherein said operative tip is an activatable device taken from the group consisting of scissors, clamps, dissectors, staplers, clip appliers, retrieval bags, and electrocautery devices, further comprising activating said operative tip after the passing of said surgical instrument through said cannula or trocar sleeve.

\* \* \* \* \*

UNITED STATES PATENT AND TRADEMARK OFFICE
CERTIFICATE OF CORRECTION

PATENT NO.   : 6,454,783 B1                                                                 Page 1 of 1
DATED        : September 24, 2002
INVENTOR(S)  : Piskun, Gregory It is certified that error appears in the above-identified patent and that said Letters Patent is hereby corrected as shown below:

<u>Title page,</u>
Insert the following priority claim under 35 U.S.C. § 119:
-- Related U.S. Application Data
 [60]   Provisional application No. 60/100,823, Sept. 15, 1998. --

Signed and Sealed this

Fifteenth Day of April, 2003

JAMES E. ROGAN
*Director of the United States Patent and Trademark Office*